United States Patent [19]

Kanazawa et al.

[11] Patent Number: 5,201,317
[45] Date of Patent: Apr. 13, 1993

[54] DIAGNOSTIC AND THERAPEUTIC CATHETER

[75] Inventors: Shin-ichi Kanazawa; Koro Yotsuya; Ichiro Sogawa; Takafumi Uemiya; Shin-ichiro Niwa, all of Osaka, Japan

[73] Assignee: Sumitomo Electric Industries, Ltd., Osaka, Japan

[21] Appl. No.: 943,141

[22] Filed: Sep. 10, 1992

Related U.S. Application Data

[63] Continuation of Ser. No. 465,072, Feb. 6, 1990, filed as PCT/JP89/00570, Jun. 6, 1989, abandoned.

[30] Foreign Application Priority Data

Jun. 6, 1988 [JP] Japan .................................. 63-138755

[51] Int. Cl.⁵ .................................................. A61B 6/00
[52] U.S. Cl. ......................................... 128/665; 606/15
[58] Field of Search .................... 128/665, 634; 606/7, 606/15-18, 192, 194

[56] References Cited

U.S. PATENT DOCUMENTS

| | | | |
|---|---|---|---|
| 3,136,310 | 6/1964 | Meltzer | 128/634 |
| 3,335,715 | 8/1967 | Hugenholtz et al. | 128/634 |
| 3,866,599 | 2/1975 | Johnson | 128/634 |
| 4,587,972 | 5/1986 | Morantte, Jr. | 606/15 |
| 4,718,423 | 1/1988 | Willis et al. | 128/634 |
| 4,768,858 | 7/1988 | Hussein et al. | |
| 4,776,340 | 10/1988 | Moran et al. | 128/634 |
| 4,961,738 | 10/1990 | Mackin | 606/15 |

FOREIGN PATENT DOCUMENTS

| | | |
|---|---|---|
| 0263645 | 4/1988 | European Pat. Off. |
| 3447642 | 9/1986 | Fed. Rep. of Germany |
| 51-72194 | 6/1976 | Japan |
| 63-95064 | 4/1988 | Japan |
| 1284537 | 8/1972 | United Kingdom |

OTHER PUBLICATIONS

Fox et al., PCT application WO 87/01273 publishing date 12 Mar. 1987.

Primary Examiner—Lee S. Cohen
Assistant Examiner—Jeffrey R. Jastrzab
Attorney, Agent, or Firm—Cushman, Darby & Cushman

[57] ABSTRACT

A diagnostic and therapeutic catheter accommodating a plurality of optical fibers and tubes, including a small diameter portion formed at a distal end portion of the catheter, the small diameter portion having at least one duct, the optical fibers and the tubes confronting an inlet of the small diameter portion so as to be retractably inserted into the small diameter portion selectively.

2 Claims, 1 Drawing Sheet

DIAGNOSTIC AND THERAPEUTIC CATHETER

This is a continuation of application Ser. No. 07/465,072, filed on Feb. 6, 1990, filed as PCT/JP89/00570, Jun. 6, 1989, now abandoned.

DESCRIPTION

1. TECHNICAL FIELD

The present invention generally relates to diagnostic and therapeutic catheters and more particularly, to a diagnostic and therapeutic catheter which is useful for performing endoscopy of vasa of living organisms, for example, blood vessels, oviducts, ureter, etc. or removing diseased parts in vasa by using laser beams.

2. BACKGROUND ART

A diagnostic and therapeutic catheter is known into which optical fibers and tubes necessary for performing diagnosis and therapy are inserted alternately.

For example, in order to perform diagnosis and therapy of a diseased part in a blood vessel, an optical fiber for endoscopy and an optical fiber for illumination are initially inserted into the catheter and a balloon for securing a distal end portion of the catheter and for stopping blood flow, which is provided at the distal end portion of the catheter, is inflated so as to stop blood flow in the blood vessel. Then, liquid (flushing liquid) whose optical loss is small in a range of wavelength of laser beams in use is fed into the blood vessel so as to replace blood in the blood vessel such that a clear view in the blood vessel is obtained. At this time, a state in the blood vessel is displayed on a screen. Subsequently, when the diseased part in the blood vessel is found, endoscopy is stopped and the optical fiber for endoscopy is replaced by an optical fiber for irradiating laser beams. Thus, in this state, laser beams are irradiated onto the diseased part by the optical fiber for irradiating laser beams so as to remove the diseased part.

At this time, since stoppage of blood flow should be limited to a short time period in view of safety of the living organism, the above replacement of the optical fibers should be performed rapidly after endoscopy. Hence, if a long time is required for making the replacement of the optical fibers, stoppage of blood flow by the balloon should be cancelled and the operations which have been performed until then are required to be performed again.

Therefore, it may be appropriate to employ a catheter of a type in which a plurality of optical fibers and tubes are preliminarily accommodated up to a distal end portion of the catheter and diagnosis and therapy of a diseased part are performed by inserting the distal end portion of the catheter to vicinity of the diseased part. However, this catheter becomes large in diameter. Thus, this catheter has such a drawback that the catheter can be inserted into relatively thick vasa but cannot be inserted into thin vasa.

An object of the present invention is to provide, in view of the above described inconveniences, a diagnostic and therapeutic catheter by which diagnosis and therapy based on the above described operational procedures can be rapidly and positively performed even in thin vasa.

DISCLOSURE OF INVENTION

In order to accomplish this object, a diagnostic and therapeutic catheter according to the present invention accommodates a plurality of optical fibers and tubes, comprising: a small diameter portion which is formed at a distal end portion of the catheter; the small diameter portion having at least one duct; the optical fibers and the tubes confronting an inlet of the small diameter portion so as to be retractably inserted into the small diameter portion selectively.

In the catheter of the above described arrangement, a plurality of the optical fibers and tubes, which become required to be used sequentially, can be preliminarily set in a waiting state at a location relatively adjacent to a diseased part in a thin vas. Therefore, in case of necessity, a necessary one of the optical fibers and tubes can be selectively drawn close to the diseased part immediately by using the duct.

BEST MODE FOR CARRYING OUT THE INVENTION

Figure 1:
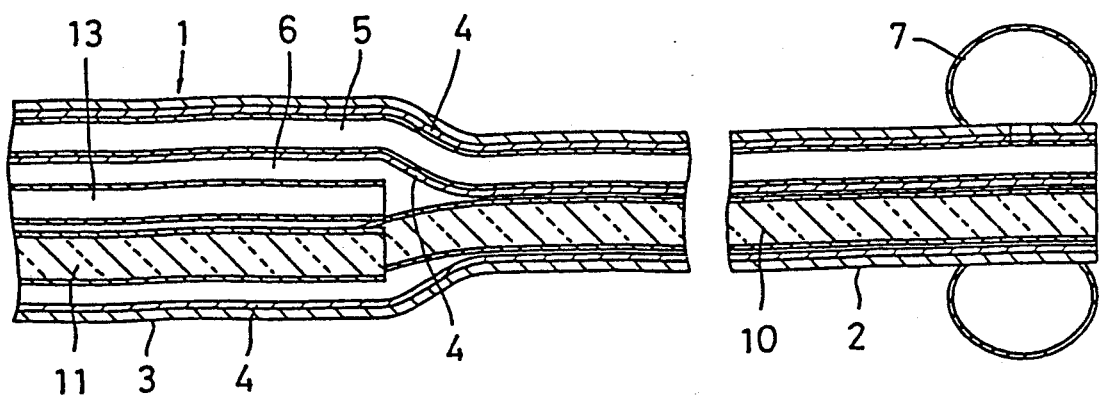
FIG. 1 is a longitudinal sectional view of a diagnostic and therapeutic catheter of the present invention.

Hereinbelow, one embodiment according to the present invention will be explained by referring to the drawings. FIG. 1 is a sectional view of a diagnostic and therapeutic catheter 1 (referred to as a "catheter", hereinbelow) according to the present invention.

Figure 2:
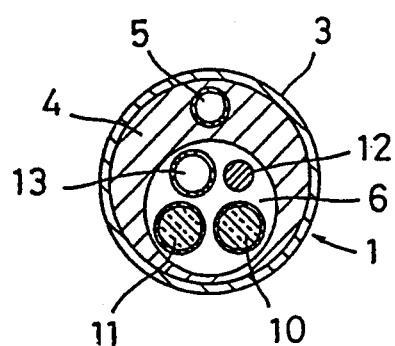
FIG. 2 is a transverse sectional view of a large diameter portion of the diagnostic and therapeutic catheter.

In FIG. 1, the catheter 1 includes a small diameter portion 2 of 10 to 20 cm in length. In the catheter 1, there are provided two ducts 5 and 6 extending continuously from a distal end of the small diameter portion 2 rearwards to a large diameter portion 3. A light guide 4 for illumination is formed in the catheter 1 so as to occupy a gap between peripheral surfaces of the ducts 5 and 6 (see FIGS. 2 and 3).

The duct 5 is formed smaller in diameter than the duct 6 and is passed through the small diameter portion 2 at an identical diameter. The duct 5 is used as a gas passage for supplying gas to a balloon 7 fixed at the distal end of the small diameter portion 2.

The duct 6 is formed larger in diameter than the duct 5. The duct 6 is so formed in the small diameter portion 2 as to easily receive any one of an optical fiber 10 for transmitting laser beams, an image optical fiber 11 for endoscopy, a wire 12 for controlling the distal end portion, a passage 13 for discharging blood and supplying flushing liquid in place of blood, etc., which are accommodated in the catheter (see FIG. 3). On the other hand, the duct 6 is so formed in the large diameter portion 3 as to simultaneously receive the optical fiber 10, the image optical fiber 11, the wire 12, the passage 13, etc.

Figure 3:
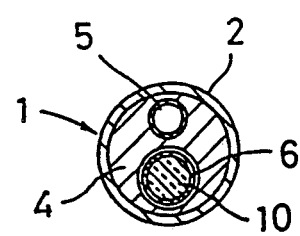
FIG. 3 is a transverse sectional view of a small diameter portion of the diagnostic and therapeutic catheter.

At a location which confronts an inlet of the small diameter portion 2 forwards from the duct 6, the optical fiber 10, the image optical fiber 11, the wire 12, the passage 13, etc. are retractably inserted into the duct in the small diameter portion 2 selectively. In this embodiment, the optical fiber 10 for transmitting laser beams is inserted from the inlet of the small diameter portion 2 to the distal end of the small diameter portion 2 so as to be used for performing laser therapy from the distal end adjacent to a diseased part as shown in FIGS. 1 and 3 (see FIG. 3).

In the diagnostic and therapeutic catheter of the above described arrangement, as shown in FIG. 1, a plurality of the optical fibers and tubes, which are required to be used sequentially, can be preliminarily set in a waiting state at a location relatively adjacent to a diseased part in a thin vas. Thus, in case of necessity, only a necessary one of the optical fibers and tubes can be retractably inserted into the small diameter portion 2 selectively and immediately so as to be drawn close to the diseased part through common use of one duct.

Meanwhile, in the above embodiment, the catheter provided with the balloon for securing the catheter and for stopping blood flow has been described. Therefore, in the small diameter portion of the catheter, the duct as the gas passage for the balloon and the duct for the optical fiber for transmitting laser beams, etc. are juxtaposed. However, in case of diagnosis and therapy of a diseased part in a minute vas, this balloon becomes unnecessary. In this case, the duct as the gas passage for the balloon can be eliminated, so that only one duct for the optical fiber for transmitting laser beams, etc. may be formed in the small diameter portion of the catheter and thus, the catheter at the small diameter portion can be further reduced in diameter. The design of the diagnostic and therapeutic catheter of the present invention can be modified variously without departing from the scope of the present invention.

In accordance with the diagnostic and therapeutic catheter of the present invention, only a necessary one of the optical fibers and tubes can be retractably inserted from the large diameter portion into the small diameter portion selectively and immediately so as to be drawn close to the target diseased part through common use of at least one duct. Accordingly, the catheter of the present invention can achieve such a characteristic effect that diagnosis and therapy based on the ordinary operational procedures can be performed rapidly and positively even in case of a thin vas.

We claim:

1. A diagnostic and therapeutic catheter comprising:
   a small diameter catheter portion which is formed at a distal end portion of said catheter, said small diameter catheter portion having at least one duct;
   a large diameter catheter portion connected to said small diameter catheter portion, said large diameter catheter portion having at least one duct coupled to said at least one duct of said small diameter catheter portion; and
   a plurality of optical fibers and tubes contained within said at least one duct of said large diameter catheter portion, said tubes and fibers being retractably insertable into said at least one duct of said small diameter catheter portion selectively, said at least one duct of said small diameter catheter portion being of a size so as to exclude a simultaneous insertion of all of said fibers and tubes contained within said at least one duct of said large diameter catheter portion.

2. A diagnostic and therapeutic catheter comprising:
   a small diameter catheter portion which is formed at a distal end portion of said catheter, said small diameter catheter portion having at least one duct;
   a large diameter catheter portion connected to said small diameter catheter portion, said large diameter catheter portion having at least one more duct than said small diameter catheter portion coupled to said at least one duct of said small diameter catheter portion; and
   a plurality of optical fibers and tubes contained within said at least one more duct of said large diameter catheter portion, said tubes and fibers being retractably insertable into said at lest one duct of said small diameter catheter portion selectively, said at least one duct of said small diameter catheter portion being of a size so as to exclude simultaneous insertion of all of said fibers and tubes contained within said at least one more duct of said large diameter catheter portion.

* * * * *